(12) United States Patent
Zhang et al.

(10) Patent No.: US 8,116,849 B2
(45) Date of Patent: Feb. 14, 2012

(54) NON-INVASIVE TEMPERATURE SCANNING AND ANALYSIS FOR CARDIAC ISCHEMIA CHARACTERIZATION

(75) Inventors: Hongxuan Zhang, Schaumburg, IL (US); Myrtis Randolph, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1078 days.

(21) Appl. No.: 11/958,730

(22) Filed: Dec. 18, 2007

(65) Prior Publication Data

US 2009/0043223 A1  Feb. 12, 2009

Related U.S. Application Data

(60) Provisional application No. 60/954,648, filed on Aug. 8, 2007.

(51) Int. Cl.
*A61B 5/05* (2006.01)

(52) U.S. Cl. ......... 600/428; 600/407; 600/425; 600/426; 600/427; 600/429; 378/1; 378/4; 378/17; 378/21; 378/51; 378/62

(58) Field of Classification Search ............... 600/407, 600/481, 549, 425–429; 374/43, 161; 702/130, 702/134, 136; 378/1, 4, 17, 21, 51, 62
See application file for complete search history.

(56) References Cited

U.S. PATENT DOCUMENTS

| | | | |
|---|---|---|---|
| 6,066,094 A * | 5/2000 | Ben-Haim | 600/437 |
| 6,490,478 B1 | 12/2002 | Zhang et al. | |
| 6,773,159 B2 | 8/2004 | Kim et al. | |
| 7,056,011 B2 | 6/2006 | Pesach | |
| 7,904,145 B2 * | 3/2011 | Hashimshony et al. | 600/547 |
| 2005/0004476 A1 * | 1/2005 | Payvar et al. | 600/481 |
| 2007/0129639 A1 | 6/2007 | Zhang | |

OTHER PUBLICATIONS

D. Tznoni, A. Cribier, K. Kanmatsuse, C. Chew and W. Ganz, "Evaluation of changes in epicardial blood flow in experimental animals by cardiothermography", European Heart Journal, 1982, Vo1.3, No. 4, pp. 382-388.

Nawata Yutaka , Yamashita Tohru , Namisaki Kousuke, "Noninvasive Measurement of Temperature Distribution in Tissues by Ultrasonic CT", Proceedings of Thermal Engineering Conference, The Japan Society of Mechanical Engineers, V 01.2005(Nov. 2, 2005), pp, 25-26.

Y. Ishihara, Y. Endo, N. Wadamori, H. Ohwada; "A Noninvasive Temperature Measurement Regarding the Heating Applicator Based on a Reentrant Cavity", STM (Society for Thermal Medicine) 2007 Annual Meeting, May 13-17, 2007, Washington Hilton, Washington, DC.

* cited by examiner

*Primary Examiner* — James Kish
(74) *Attorney, Agent, or Firm* — Alexander J Burke

(57) ABSTRACT

A method is disclosed for achieving improved quality of monitoring and diagnosis for heart functions. Specifically, a method is disclosed for continuous temperature measurement and thermal characterization of patient heart tissue based on non-invasive thermal mapping technology. The method includes multi-dimensional cardiac tissue temperature scanning and tissue thermal pattern analysis with high precision, which can greatly improve the efficiency and lower the medical procedure risk for identifying myocardial ischemia (MI) disorders, predicting the MI occurrence, and mapping MI characteristics and impacting MI medical treatment, such as drug delivery and long term cardiac care. A system is also disclosed for use with the method.

20 Claims, 3 Drawing Sheets

NON-INVASIVE TEMPERATURE SCANNING AND ANALYSIS FOR CARDIAC ISCHEMIA CHARACTERIZATION

CROSS-REFERENCE TO RELATED APPLICATIONS

This is a U.S. non-provisional application of U.S. provisional patent application Ser. No. 60/954,648, filed Aug. 8, 2007, by Hongxuan Zhang et al, the entirety of which application is incorporated herein by reference.

FIELD OF THE DISCLOSURE

The disclosure relates to systems and methods for non-invasive measurement and characterization of patient tissue, and more particularly to methods for continuous temperature measurement and thermal characterization of cardiac tissue based on non-invasive thermal mapping.

BACKGROUND

The most frequent killer of Americans is coronary artery disease (CAD) and heart-related problems. The principal manifestations of CAD are coronary artherosclerosis (hardening of the coronary arteries) and stenosis (narrowing of the arteries), both of which ultimately force a reduction of flow to the coronary circulation (myocardial ischemia). An ischemic episode (either due to severe narrowing, or artery blockage) generally leads to angina pectoris, or a heart attack. During ischemia, various portions of heart muscle receive less oxygen which can ultimately lead to irreversible scarring and necrosis of the muscle tissue (myocardial infarction), reducing the efficiency with which the heart can pump blood to the rest of the body and possibly leading to fatal cardiac arrhythmias.

Recent research indicates that temperature monitoring and thermal pattern analysis of the cardiac tissue may provide more a precise qualitative and quantitative methodology to analyze the heart pathologies and functional status. Clinically, an electrophysiology (EP) catheter with a thermister at its tip is often used to monitor the myocardial tissue temperature for safety purposes during procedures such as atrial fibrillation ablation procedures. Although significant progress has been made in the electrophysiology analysis of cardiac arrhythmia, especially cardiac ischemia and infarction, there are several shortcomings with the current state of the art.

First, there are no non-invasive methods available for continuous temperature measuring, monitoring and mapping of the heart and circulation system. Thermister-based measurement using an EP catheter has limited measuring precision and accuracy, and also carries the potential risk of catheter position switching, as well as unreliable continuous measuring.

Second, current thermal scanning and monitoring techniques, such as using an intra-cardiac thermister, cannot provide the high resolution required for precise temperature measurement of cardiac tissue or for precise cardiac tissue localization. Further problems may include inaccurate operation procedure grasping and time synchronization (i.e., the simultaneous conformity of heart rate and blood flow in a patient's heart) and myocardial infarction (MI) emerging and recovering, which relate to the development of a potential myocardial infarction (a heart attack) and the uncertainty of when a heart attack may be about to occur, or whether the heart will be able to heal from a heart attack or will be irreparably damaged.

Third, current cardiac tissue temperature monitoring using a catheter/thermister is typically focused on single point/position. As a result, it cannot provide real time 2D and 3D continuous thermal mapping and scanning of cardiac tissue.

Fourth, there are no methods currently available for electrophysiological function analysis correlated heart tissue thermal monitoring and diagnosis.

Fifth, there are no multi-dimensional temperature and thermal pattern analyses for ischemia recognition and diagnosis, for example pecutaneous transluminal coronary angioplasty (PTCA) procedure monitoring, or long term monitoring of the growth of myocardial ischemia and infarction of heart tissue, ischemic/infarcted size, pathological tissue border, volume and pathology/healthy index analysis.

Thus, there is a need for a temperature scanning and pattern analysis-based method for cardiac tissue monitoring for clinical applications, since cardiac tissue thermal analysis and mapping is correlated to blood flow in the cardiac chambers and tissues. Further determinations may be made using such a method, including blood flow speed, volume per heart beat, and the like, especially for the left ventricle.

SUMMARY

The disclosed system and technique may solve the aforementioned shortcomings, providing a safer, more accurate, and more efficient method and strategy for cardiac tissue monitoring and diagnosis. The versatile multi-dimensional temperature scanning, mapping and thermal pattern characterization system and technique may provide a precise approach for identifying cardiac disorders, predicting cardiac pathology occurrence, and mapping cardiac malfunction characteristics, thereby providing improved input for medical decision making and clinical treatment, including decisions regarding drug delivery and long term cardiac care. Furthermore, the automatic non-invasive thermal pattern mapping strategy can greatly reduce the cost of the medical diagnosis and treatment, and improve the stability and reliability of the corresponding clinical application.

A method for non-invasive temperature measurement of tissue is disclosed, comprising measuring a plurality of permittivity values associated with portions of a tissue segment; converting said plurality of permittivity values to a plurality of associated temperature values; developing a temperature map of said tissue segment using said plurality of associated temperature values; comparing said plurality of associated temperature values against one or more predetermined temperature values; determining, based on said comparing step, whether an abnormal temperature pattern exists; and providing a user warning if said abnormal temperature pattern is determined; wherein the step of developing a temperature map further comprises synchronizing the temperature values with measured electrocardiogram (ECG) signals using ECG signal gating.

A system for non-invasive temperature measurement of tissue is disclosed, comprising means for measuring a plurality of permittivity values associated with portions of a tissue segment; means for converting said plurality of permittivity values to a plurality of associated temperature values; means for developing a temperature map of said tissue segment using said plurality of associated temperature values; means for comparing said plurality of associated temperature values against one or more predetermined temperature values; means for determining, based on said comparing step, whether an abnormal temperature pattern exists; and means for providing a user warning if said abnormal temperature pattern is determined; wherein the means for developing a temperature map further comprises means for synchronizing the temperature values with measured electrocardiogram (ECG) signals using ECG signal gating.

A machine readable storage device tangibly embodying a series of instructions executable by the machine to perform a series of steps is also disclosed, the steps comprising: measuring a plurality of permittivity values associated with portions of a tissue segment; converting said plurality of permittivity values to a plurality of associated temperature values; developing a temperature map of said tissue segment using said plurality of associated temperature values; comparing said plurality of associated temperature values against one or more predetermined temperature values; determining, based on said comparing step, whether an abnormal temperature pattern exists; and providing a user warning if said abnormal temperature pattern is determined; wherein the step of developing a temperature map further comprises synchronizing the temperature values with measured electrocardiogram (ECG) signals using ECG signal gating.

BRIEF DESCRIPTION OF THE DRAWINGS

The accompanying drawings illustrate preferred embodiments of the disclosed system and technique so far devised for the practical application of the principles thereof, and in which.

DETAILED DESCRIPTION

The disclosed system and method can provide a safer, more accurate, and more efficient method and strategy for cardiac tissue monitoring and diagnosis. The versatile multi-dimensional temperature scanning, mapping and thermal pattern characterization technique may provide a precise approach for identifying cardiac disorders, predicting cardiac pathology occurrence, and mapping cardiac malfunction characteristics, as well as providing better input for medical decision making and clinical treatment such as drug delivery and long term cardiac care. Furthermore, the automatic non-invasive thermal pattern mapping strategy can greatly reduce the cost of the medical diagnosis and treatment, and can improve the stability and reliability of corresponding clinical application. The disclosed system and method can be used to monitor and diagnose the pathologies and malfunctions of the heart tissue during other cardiac arrhythmias, such as atrial fibrillation and ventricle tachycardia.

New development of computer technology and medical devices, such as those for non-invasive multi-dimensional scanning, make it possible to achieve more comprehensive and precise mapping and analysis for real time cardiac monitoring, especially in cardiac arrhythmia calculation, characterization, diagnosis, prediction, and medical treatment.

1. Non-invasive Temperature Measurement, Scanning and Mapping Technologies

Non-invasive temperature measurement is based on the permittivity change of cardiac tissue accompanying a temperature change. In order to measure a temperature change precisely, the phase change of the electric field inside the reentrant cavity (i.e., the chamber of the heart in which the electrical activity re-occurs and is actively creating electrical changes in the circuit of the heart), which is produced as a result of a change in tissue permittivity, is detected.

In the applicator 4 based on the reentrant cavity, an electric field distribution is formed toward the opposed reentrant gap. As noted, the reentrant cavity is the heart chamber where the electrical activity of the heart takes place. The reentrant gap refers to the output received from the heart tissue, and is described in Y. Ishihara, Y. Endo, N. Wadamor, H. Ohwada; "A Noninvasive Temperature Measurement Regarding the Heating Applicator Based on a Reentrant Cavity," STM (Society for Thermal Medicine) 2007 Annual Meeting, May 13-17, 2007, Washington Hilton, Washington, D.C., the entirety of which is incorporated by reference herein.

Figure 1:
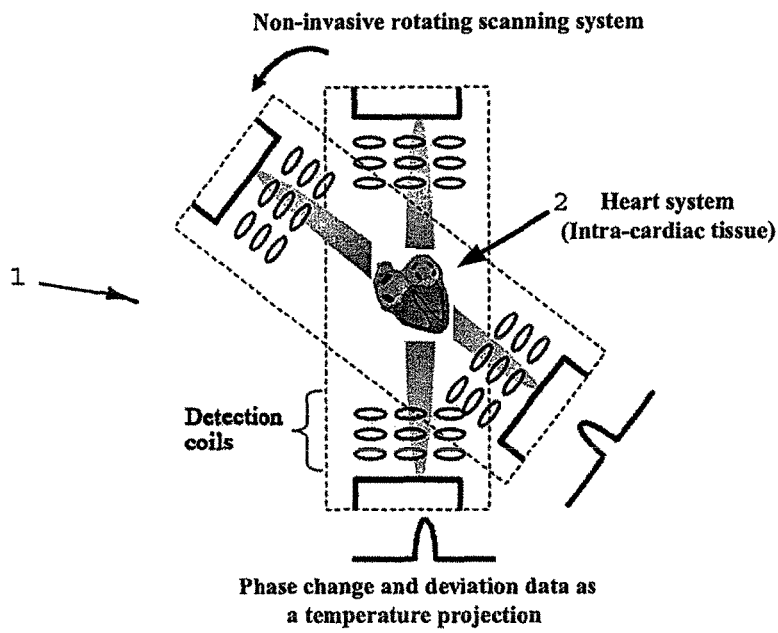
FIG. 1 illustrates a system for the disclosed intra-cardiac tissue temperature measurement.

Referring to FIG. 1, when subject tissue 2, which in the illustrated embodiment is patient heart tissue, is inserted and the temperature of the heart increases in this reentrant gap due to an increase in blood flow, the phase change accompanying a temperature change mainly appears in the region along the direction of the electric field. As a result, a change in the temperature distribution can be estimated using techniques such as X-ray CT by detecting the phase change of the subject tissue 2 and rotating the applicator 4 about the tissue 2. In one embodiment, an electromagnetic field distribution accompanying a temperature change is analyzed, a computed tomography (CT) algorithm is used based on the data of the calculated phase change, and a temperature change is estimated. Any appropriate CT algorithm (e.g., threshold algorithm) can be utilized for the data calculation and data fusion to integrate the CT scanning and phase changes. The temperature changes in the tissue are based on the scanning and phase changes. In one non-limiting example, a knowledge based CT algorithm may be utilized for identification, computation and classification of the temperature mode. Based on the permittivity measurement, temperature may be derived using any of a variety of known algorithms (e.g., Onsager's equation and neural network algorithms).

FIG. 1 shows the basic structure for the intra-cardiac tissue temperature measurement system 1. The system 1 can provide 3-D thermal structure of the intra-cardiac tissue 2 by rotating (XYZ, 3D orientations), scanning and mapping. Permittivity of the tissue is scanned in a similar manner and method as X-ray scanning. The tissue is scanned using CT which allows for images to be generated in various planes and/or in three dimensions. X-ray slice data is generated using an X-ray source that rotates around the object. X-ray sensors are positioned on the opposite side of the circle from the source. Numerous data scans are progressively taken as the subject is gradually passed through the gantry. These scans are combined using tomographic reconstruction to obtain the desired images.

In one embodiment, the cardiac tissue temperature measuring and scanning system 1 can be synchronized and adaptively controlled with electrocardiogram (ECG) signal gating. When dealing with rigid tissue, typically the temperature scanning and CT algorithm do not need synchronization. When dealing with soft tissue, however, such as heart tissue, a synchronization mode and strategy may be used to acquire stable scanning results and reliable temperature analysis. The CT scanning and related analysis may be applied to the heart in its resting stages. Because the heart and circulatory vessels (including the blood flowing therethrough) are not rigid materials and are in motion, performing the scanning during the resting phase may provide the most stable scanning and image/position registration. Blood flow itself may provide wide signal variability (temperature and thermal data), and during the resting stage the data variability is typically very low, thus resulting in better data quality in scanning, measuring, mapping and diagnosis. Without stable scanning and image/position registration, the sensitivity, accuracy, stability and resolution of the temperature and thermal mapping and analysis output may be greatly reduced, resulting in noisy and distorted temperature output and potentially inaccurate medical interpretation. ECG signal gating may be implemented to enhance stability and accuracy of the scanning. The gating strategies may be accomplished adaptively with synchronizing the CT algorithm with the ECG signals.

The ECG signal gated X-ray scanning and phase change based thermal monitoring can avoid errors caused by the normal depolarization and repolarization of the heart, which may result in inaccurate localization of cardiac tissue position and acquired signal distortion. The non-invasive rotating scanning and thermal measuring system 1 may include any of a variety of known three dimensional robotic and automation technologies to control and steer the device rotation and scanning, including scanning power, angle, time, etc.

Scanning and temperature acquisition may further comprise automatic and adaptive technologies for controlling the scanning focus in the cardiac tissue, which may provide high resolution and accuracy in temperature calculation, tissue localization, and malfunction tissue border analysis, especially in the ischemia analysis.

2. Temperature Pattern Analysis and 3D Cardiac Thermal Modeling for Myocardial Ischemia Analysis a. Single Point Temperature Pattern Analysis Traditional method for detecting a myocardial ischemia and infarction relies on the electrophysiology analysis, such as ST segment changes in the surface electrophysiological activity (ECG) signals. Unfortunately, there are many cases of myocardial ischemia (MI) processes that such traditional methodologies cannot help. For example, non-symptom ischemia (no pain and no obvious electrophysiological change), and even some ischemia with minute cardiac tissue, cannot reliably be captured and localized by traditional methods.

Figure 2:
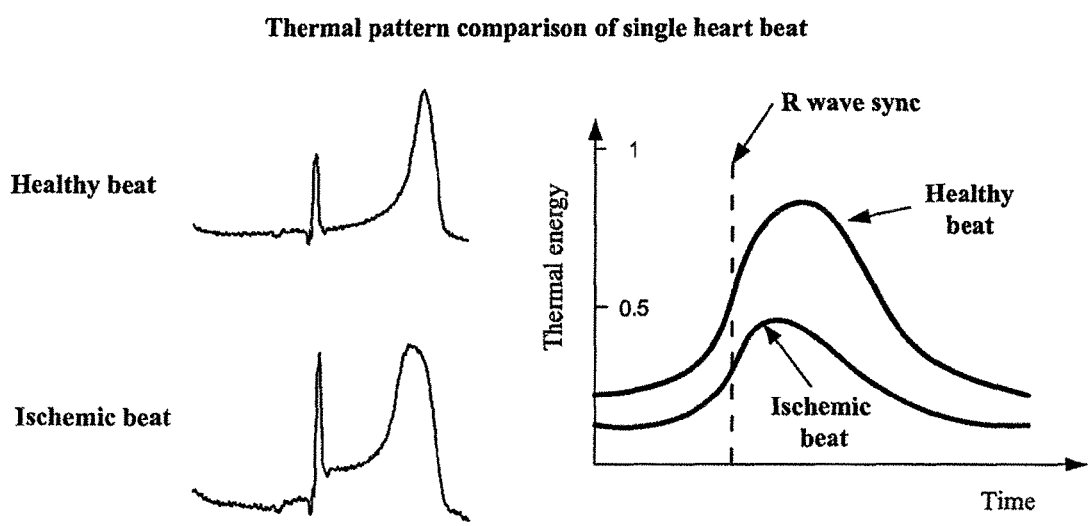
FIG. 2 illustrates a comparison of the temperature characteristics with time for an ischemic heart beat and a healthy heart beat.

In one embodiment of the disclosure, temperature and thermal patterns are analyzed by beat units such that minute changes due to blood flow and pathology can be identified. Referring to FIG. 2, a comparison of the temperature characteristics with time for two heart beats is shown: an ischemic heart beat and a healthy heart beat. In the comparison, the ischemic beat has a lower thermal energy curve than a normal heart beat, due to the lower blood flow associated with cardiac tissue ischemia. This thermal function pattern comparison can be utilized to qualitatively and quantitatively characterize the ischemia event and to aid in medical treatment determinations. As a comparison, the ECG and thermal energy signals of a healthy heart and an ischemic heart are shown in FIG. 2.

A typical method for identifying myocardial ischemia is to measure the ST segment displacements and changes of the heart, for example, 0.1 millivolt (mV) as a criteria and threshold for surface ECG signal ST segment change. However, electrophysiological activity is not always true and sensitive to the early stage of MI process and some long term non-symptom ischemia. By contrast, the thermal and temperature pattern analysis in one embodiment of the disclosure can be utilized for any kind of ischemia, thus providing high reliability and sensitivity for cardiac pathology detection and analysis.

Figure 3:
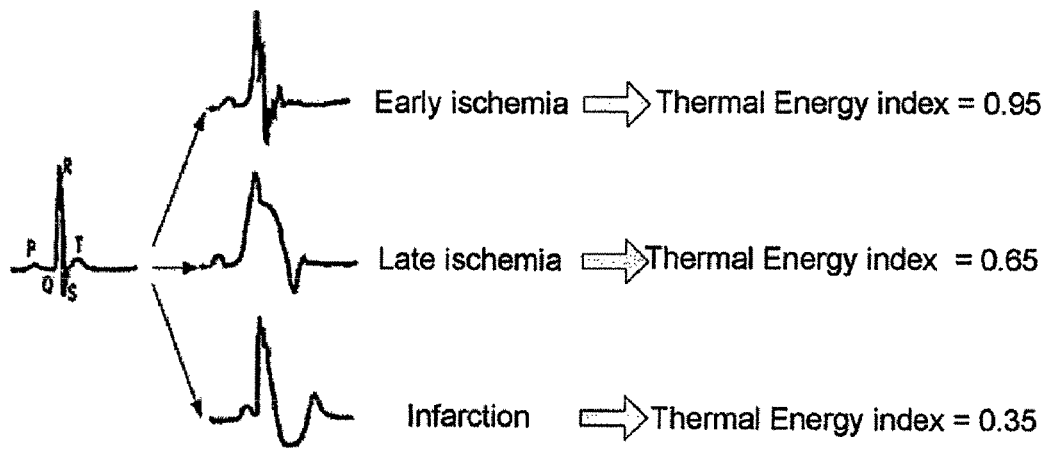
FIG. 3 illustrates a comparison of electrophysiology and thermal pattern analysis results during an exemplary Pecutaneous Transluminal Coronary Angioplasty (PTCA) procedure.

In one embodiment, thermal pattern analysis is used for real time monitoring of the cardiac tissue, heart function, medical procedure monitoring, such as PTCA procedure monitoring and cardiac tissue safety monitoring in atrial fibrillation (AF) ablation. One application example is shown in FIG. 3, which illustrates a comparison of electrophysiology and thermal pattern analysis results during a PTCA procedure. Early ischemia, late ischemia and possible infarction processes are compared in the figure. The electrophysiological analysis, such as ST segment displacement, is subject to the medical criteria and doctor's interpretation. However thermal energy index of the ROI ("region of interest," which in this case is the possible ischemia area) shows the clear and stable results of the cardiac tissue during the PTCA procedure. In the illustrated case, a non-subjective calculated thermal energy index clearly correlates with the degree of ischemia or infarction in the subject tissue.

b. Multi-dimensional (2D and 3D) Cardiac Thermal Mapping and Ischemia Analysis

Figure 4:
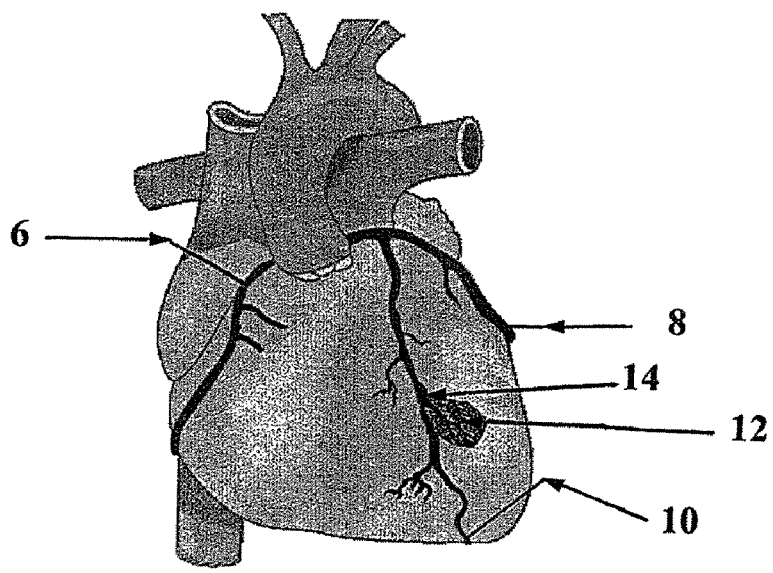
FIG. 4 illustrates a 3D thermal map for use in ischemic and infarcted heart analysis.

In order to capture and characterize more details and information regarding particular cardiac pathologies, multi-dimensional thermal mapping and scanning strategies may be utilized for the heart and its blood circulation system. FIG. 4 shows a 3D thermal map for ischemic cardiac tissue analysis. There are 3 main arteries vessel in the heart muscle: right coronary artery (RCA) 6, left circumflex artery (LCA) 8, and left artery descending (LAD) 10. The LAD artery branch 10 is important since it provides blood to left ventricle, and thus any kind of ischemia/infarction in this branch may result in chest pain, artery blockage, or tissue damage, and in the worst cases cardiac arrest and death.

FIG. 4 is a 3D thermal map of ischemic and infarcted heart analysis. In the second diagonal of LAD artery branch 10, there is a small area 12 with ischemia, low blood flow region, associated with block point 14. For the pictured tissue, the occlusion will affect the cardiac circulation, like the APs (action potentials) generation and transmission in the corresponding occlusion area, like excitation impulse block in the bundle of His (the collection of heart muscle cells specialized for electrical conduction that transmits the electrical impulses from the AV node (located between the atria and the ventricles) to the point of the apex of the fascicular branches), and the bundle Branches. With prior techniques such as surface ECG and intra-cardiac electrograms, this kind of minute ischemic region might not be efficiently and correctly captured and characterized. With 3D thermal scanning and mapping, however, the size, thickness, and border can be characterized with high resolution imaging such that appropriate medical treatment can be quickly and efficiently applied to the affected cardiac tissue to minimize the chance for further tissue damage.

Multi-dimensional thermal and temperature scanning and mapping may be especially helpful in the long term monitoring and diagnosis for MI patients. Several thermal mapping images can be obtained over time and compared to identify time-based changes in the ischemic tissue, as well as to identify growth in the affected "malfunctioning" region.

Figure 5:
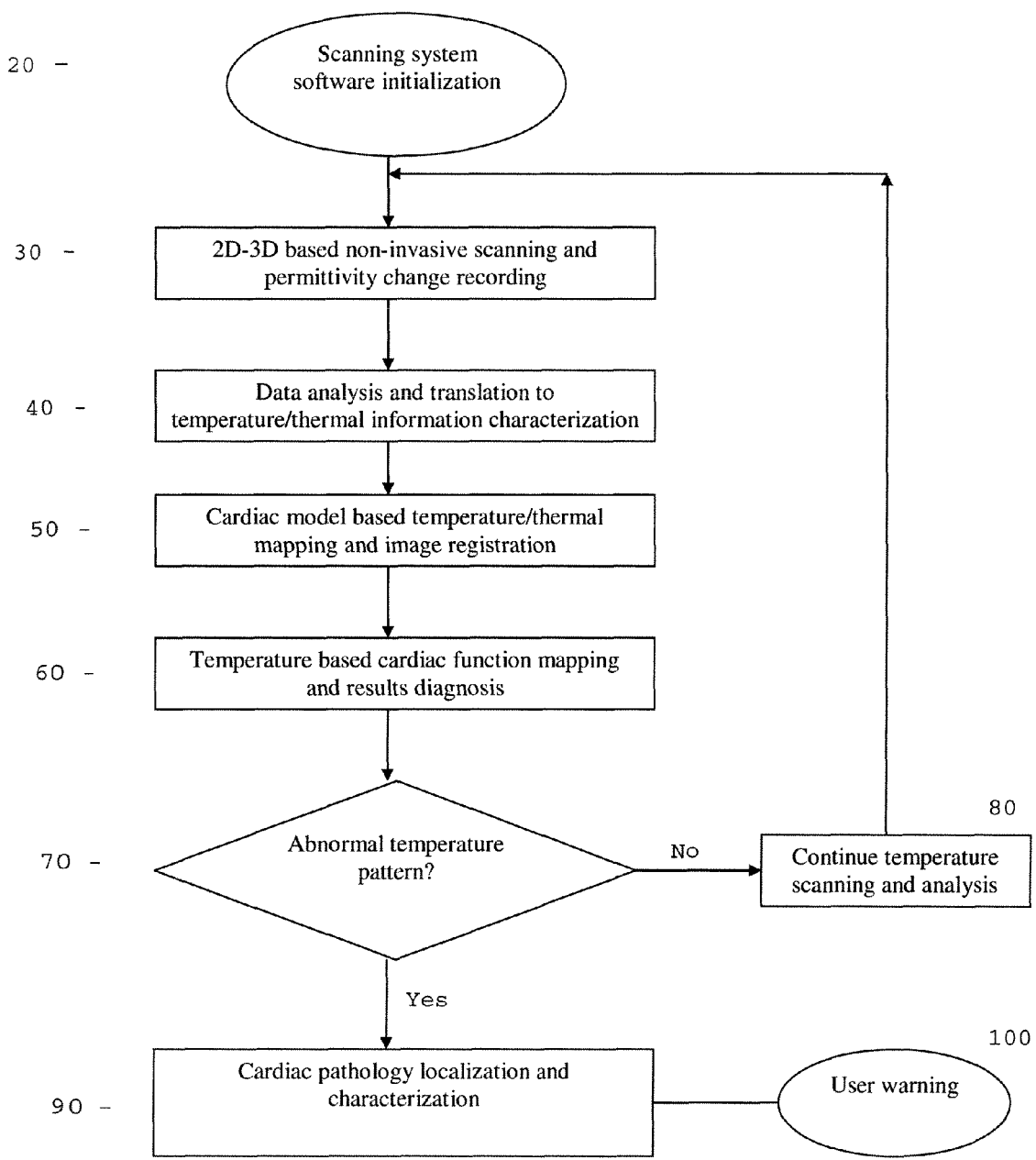
FIG. 5 is a flowchart describing the disclosed method.

Referring now to FIG. 5, an exemplary embodiment of the disclosed method is shown. At step 20, the scanning system and software is initialized. At step 30, the scanning system records permittivity change in a targeted tissue segment based on values measured from an attached CT or other data acquisition device. At step 40, the measured permittivity values are converted to temperature values. At step 50, thermal mapping and image registration based on the measured and converted temperature values is performed. At step 60, temperature-based cardiac function mapping is performed. At step 70, the system determines, based on predetermined criteria, whether an abnormal temperature pattern has been measured. If no such abnormal temperature pattern has been measured, then at step 80 the system continues with the temperature scanning and analysis, and returns to step 30 to continue the process. If, however, an abnormal temperature pattern is determined to have been measured, at step 90 the system determines cardiac pathology localization and characterization, followed by an alert to the user at step 100. Appropriate alerts may be visual, audible or a combination of both.

A variety of factors may greatly improve the temperature based cardiac function analysis and diagnosis, including permittivity to temperature mapping (e.g., artificial neural network-based analysis), heart physical structure based pathology and function characterization (e.g., image registration), and the like. If abnormal temperature or thermal patterns are determined in the analysis, localization and characterization analysis may be utilized to diagnose the details of the malfunctioning cardiac tissue, such as edge, temperature variability, region size, severity level, and the like. Based on this, function mapping-based diagnosis information and feedback may be presented to the user.

The disclosed system and method may provide feedback or other information to the user in a variety of ways, including one or more static images with temperature mapping, or dynamic imaging for location functionality (e.g., second diagonal of the LAD artery). In one example, an image similar to that shown in FIG. 4 may be used as a graphical presentation, or can be used as chart data for clinical cases. In some embodiments, the graphical display can be presented on a two-dimensional screen or a three-dimensional screen for viewing by the user.

3. Alternative Applications for Thermal and Temperature Analysis

Apart from the multi-dimensional thermal and temperature scanning and pattern analysis, the non-invasive temperature mapping system and method can be utilized in a wide variety of medical application:

A. High resolution ischemia imaging can provide an accurate gauge for sizing and positioning of stents within the affected vessel, if needed.

B. The disclosed system and method can help to construct a human body GSP system (Global Position system) which can greatly help to track any kind of pathology and malfunction of tissue and organs. GPS in this embodiment refers to tissue mapping and position localization methods and strategies. Physically, the heart structure and functions can be linked together. The temperature scanning and analysis of the disclosure can map the temperature and thermal mode to the physical cardiac structure, thus resulting in a heart "GPS" system. With mapping and tissue localization, the thermal mapping image can be registered with structure and heart function image, which may provide more precise and accurate tracking of the pathology and malfunctions for the heart and the circulation system. The techniques used for mapping image registration may be similar to those implemented in commercial systems such as the CARTO system, by Biosense Webster, Inc.

C. Blood flow tracking and diagnosis using the disclosed thermal imaging and mapping techniques can help to monitor the cardiac output for each chamber of the heart, circulation vessel, etc. Cardiac output measures the squeeze of the left ventricle and the ability of the heart to supply blood to the body. Having accurate information regarding cardiac output may thus be important because low cardiac output may mean that critical heart or lung diseases are impacting the workload of the heart.

D. Cardiac tissue analysis can be performing using 3D thermally measured tissue characteristics such as thickness, size, volume, border, and mass of the malfunctioned cardiac tissues. Using a non-invasive technique to gain information about the cardiac output of a patient's heart will enable efficient patient treatment with little or no trauma.

E. Real time thermal monitoring and mapping can help to construct a new approach to track the pathway, electrophysiological procedure and cardiac excitation conducting problem, e.g. during depolarization and repolarization of the heart. Typically, an electrophysiological activity monitoring and analysis technique is employed to track the pathway, electrophysiological procedure and cardiac excitation conducting problem. In one embodiment of the disclosure, a non-invasive temperature and thermal mapping analysis technique is used to accomplish this tracking. During heart electrophysiological conduction, the excitation pulse (i.e., depolarization and repolarization) provides the synchronization of the myocardium to contract. This can be tracked and monitored by energy transmission, such as temperature and thermal scanning. For example, a high temperature point is indicative of the excitation region. For the whole heart beat procedure, from sinoatrial (SA) node to atrioventricular (AV) node, and to the entire heart, thermal excitation mapping and conducting can be derived by temperature scanning and monitoring. Hence, the disclosed non-invasive real time thermal monitoring and mapping technique is a safer approach to cardiac function tracking, such as excitation, pathway, and the like.

F. The temperature and thermal scanning and mapping technology can be utilized in combination with ECG signal analysis and intra-cardiac electrograms analysis, as well as other hemodynamic analyses such as invasive/non-invasive blood pressure measurement, cardiac impedance measurement, and the like, to aid practitioners in diagnosing and treating a particular patient's condition in the most efficient manner practical.

G. The disclosed system and method can be used to monitor and diagnose the pathologies and malfunctions of the heart tissue during other cardiac arrhythmias, such as atrial fibrillation and ventricle tachycardia.

Advantages

The disclosed system and technique may provide the following advantages over the current techniques:

1. Non-invasive automatic temperature scanning and mapping technology will greatly improve clinical application safety, will significantly decrease the time required for cardiac function analysis, will greatly enhance the reliability and accuracy of medical application procedures and will ensure timely treatment.

2. The disclosed 3D tissue thermal imaging and mapping technology can provide precise and high resolution for temperature value, time and spatial position for monitoring cardiac tissue, especially for identifying malfunctioning tissue with accurate XYZ-3D orientations.

3. The disclosed technology can qualitatively and quantitatively characterize the thermal patterns in a single point of the cardiac tissue, in a local region of interest (ROI) such as a chamber, as well as for the entire heart. The scanning, mapping and diagnosis can be performed in real time to provide fast monitoring and analysis of targeted cardiac tissue.

4. The disclosed technology can be utilized to synchronically associate the electrophysiological function of the heart. Thus, non-invasive temperature scanning may assist the cardiologist or electro-physiologist in treating patients by providing the practitioner with information valuable for diagnosing cardiac disease, while providing methods to detect decreased tissue temperature in a patient's heart that would be indicative of diminished blood flow, and simultaneously mapping the electrical activity of the patient's heart. The temperature and thermal analysis technology may provide much earlier and better sensitivity than current electrophysiological potential analyses used during cardiac arrhythmia detection and diagnosis, particularly for MI and infarction.

5. The disclosed technology may be used to characterize minute changes in cardiac pathology such as ischemic/infarcted tissue size, pathological tissue border, volume, etc., for both acute cardiac malfunction processes and long term cardiac pathology care. Specifically, the multi-dimensional temperature and thermal pattern analysis my provide accurate monitoring and prediction in the diagnosis of silent ischemia/infarction which may occur without symptoms.

6. Similar to fluid speed analysis in ultrasound imaging technology, the disclosed technique can be utilized to monitor the blood flow in any of a variety of blood vessels and chambers, and can be used in cardiac output calculations and evaluations, and particularly for the characterization of ventricular function.

7. The disclosed technique can further be used to monitor and diagnose the pathologies and malfunctions of the heart tissue during other cardiac arrhythmias, such as atrial fibrillation and ventricle tachycardia.

The system and technique described herein may be automated by, for example, tangibly embodying a program of instructions upon a computer readable storage media, capable of being read by machine capable of executing the instructions. A general purpose computer is one example of such a machine. Examples of appropriate storage media are well known in the art and would include such devices as a readable or writeable CD, flash memory chips (e.g., thumb drive), various magnetic storage media, and the like.

The features of the system and technique have been disclosed, and further variations will be apparent to persons skilled in the art. All such variations are considered to be within the scope of the appended claims. Reference should be made to the appended claims, rather than the foregoing specification, as indicating the true scope of the subject system and technique.

What is claimed is:

1. A method for non-invasive temperature measurement of tissue, comprising:
    generating X-ray image data of a tissue segment using an X-ray image scanning system;
    measuring a plurality of permittivity values of portions of said tissue segment in response to the X-ray image data;
    converting said plurality of permittivity values to a plurality of associated temperature values;
    developing a temperature map of said tissue segment using said plurality of associated temperature values;
    comparing said plurality of associated temperature values against one or more predetermined temperature values;
    determining, based on said comparing step, whether an abnormal temperature pattern exists; and
    providing a user warning if said abnormal temperature pattern is determined;
    wherein the step of developing a temperature map further comprises synchronizing the acquisition of temperature values with a particular portion of a heart cycle using measured electrocardiogram (ECG) signals using ECG signal gating.

2. The method of claim 1, wherein measuring step comprises a two-dimensional or three-dimensional non-invasive permittivity scanning technique and
    said temperature map information is registered with a heart image.

3. The method of claim 2, wherein the measuring step further comprises using an X-ray radiation detector mounted to a controllable imaging system robotic device to enable measurements to be taken at a plurality of locations about the tissue segment.

4. The method of claim 2, wherein said steps of measuring, converting, developing, comparing and determining steps are repeated if, during said determining step, no abnormal temperature pattern exists.

5. The method of claim 4, further comprising providing a graphical output to a user, said graphical output including at least a portion of said temperature map.

6. The method of claim 5, wherein said tissue segment comprises cardiac tissue.

7. The method of claim 1, further comprising the step of using said temperature map to diagnose at least one patient condition selected from the list consisting of myocardial infarction, myocardial ischemia, atrial fibrillation and ventricle tachycardia.

8. A system for non-invasive temperature measurement of tissue, comprising:
    means for generating X-ray image data of a tissue segment using an X-ray image scanning system;
    means for measuring a plurality of permittivity values of portions of said tissue segment in response to the X-ray image data;
    means for converting said plurality of permittivity values to a plurality of associated temperature values;
    means for developing a temperature map of said tissue segment using said plurality of associated temperature values;
    means for comparing said plurality of associated temperature values against one or more predetermined temperature values;
    means for determining, based on said comparing step, whether an abnormal temperature pattern exists; and
    means for providing a user warning if said abnormal temperature pattern is determined; wherein the means for developing a temperature map further comprises means for synchronizing the acquisition of temperature values with a particular portion of a heart cycle using measured electrocardiogram (ECG) signals using ECG signal gating.

9. The system of claim 8, wherein the means for measuring comprises a two-dimensional or three-dimensional non-invasive permittivity scanning device and
    said temperature map information is registered with a heart image.

10. The system of claim 9, wherein the means for measuring comprises an X-ray radiation detector mounted to a controllable imaging system robotic device to enable measurements to be taken at a plurality of locations about the tissue segment.

11. The system of claim 8, further comprising means for providing a graphical output to a user, said graphical output including at least a portion of said temperature map.

12. The system of claim 11, wherein said means for providing a graphical output comprises a two-dimensional or three-dimensional video screen.

13. The system of claim 8, further comprising the step of using said temperature map to diagnose at least one patient condition selected from the list consisting of myocardial infarction, myocardial isehemia, atrial fibrillation and ventricle tachycardia.

14. A machine readable non-transitory storage device tangibly embodying a series of instructions executable by the machine to perform a series of steps, the steps comprising:
    measuring a plurality of permittivity values associated with portions of a tissue segment in response to X-ray radiation from an X-ray image scanning system;
    converting said plurality of permittivity values to a plurality of associated temperature values;
    developing a temperature map of said tissue segment using said plurality of associated temperature values;
    comparing said plurality of associated temperature values against one or more predetermined temperature values;
    determining, based on said comparing step, whether an abnormal temperature pattern exists; and
    providing a user warning if said abnormal temperature pattern is determined;
    wherein the step of developing a temperature map further comprises synchronizing the acquisition of temperature values with a particular portion of a heart cycle using measured electrocardiogram (ECG) signals using ECG signal gating.

15. The machine readable non-transitory storage device of claim 14, wherein measuring step comprises a two-dimensional or three-dimensional non-invasive permittivity scanning technique and said temperature map information is registered with a heart image.

16. The machine readable non-transitory storage device of claim 15, wherein the measuring step further comprises using an X-ray radiation detector mounted to a controllable imaging system robotic device to enable measurements to be taken at a plurality of locations about the tissue segment.

17. The machine readable non-transitory storage device of claim 15, wherein said steps of measuring, converting, developing, comparing and determining steps are repeated if, during said determining step, no abnormal temperature pattern exists.

18. The machine readable non-transitory storage device of claim 17, further comprising providing a graphical output to a user, said graphical output including at least a portion of said temperature map.

19. The machine readable non-transitory storage device of claim 18, wherein said tissue segment comprises cardiac tissue.

20. The machine readable non-transitory storage device of claim 14, further comprising the step of using said temperature map to diagnose at least one patient condition selected from the list consisting of myocardial infarction, myocardial ischemia, atrial fibrillation and ventricle tachycardia.

* * * * *